US009633396B2

(12) United States Patent
Hill

(10) Patent No.: US 9,633,396 B2
(45) Date of Patent: Apr. 25, 2017

(54) SYSTEMS AND METHODS FOR PREVENTING FRAUD

(71) Applicant: Vincent E. Hill, Washington, DC (US)

(72) Inventor: Vincent E. Hill, Washington, DC (US)

(73) Assignee: Fraud ID Standard Technology, Washington, DC (US)

( * ) Notice: Subject to any disclaimer, the term of this patent is extended or adjusted under 35 U.S.C. 154(b) by 203 days.

(21) Appl. No.: 13/675,142

(22) Filed: Nov. 13, 2012

(65) Prior Publication Data

US 2013/0197923 A1    Aug. 1, 2013

Related U.S. Application Data

(63) Continuation-in-part of application No. 12/978,434, filed on Dec. 24, 2010, now Pat. No. 8,311,857.

(51) Int. Cl.
| | | |
|---|---|---|
| G06Q 40/00 | (2012.01) | |
| G06Q 40/08 | (2012.01) | |
| G06Q 50/22 | (2012.01) | |
| G06Q 30/04 | (2012.01) | |
| G06Q 50/24 | (2012.01) | |

(52) U.S. Cl.
CPC ............ *G06Q 40/08* (2013.01); *G06Q 30/04* (2013.01); *G06Q 50/22* (2013.01); *G06Q 50/24* (2013.01)

(58) Field of Classification Search
CPC .... G06Q 10/10; G06Q 30/0185; G06Q 40/08; G06Q 50/22; G06Q 50/24; G06F 19/328; G06F 19/322
USPC .......................................................... 705/4
See application file for complete search history.

(56) References Cited

U.S. PATENT DOCUMENTS

| | | |
|---|---|---|
| 6,950,804 B2 | 9/2005 | Strietzel |
| 7,024,374 B1 | 4/2006 | Day et al. |
| 7,035,901 B1 | 4/2006 | Kumagai et al. |
| 7,559,018 B2 * | 7/2009 | Matti .................... G06F 17/243 715/234 |
| 7,729,929 B2 | 6/2010 | Heidenreich et al. |

(Continued)

OTHER PUBLICATIONS

Carol De Mare, S. W. (Dec. 29, 1994). Medical Equipment Principals Deny Bilking Medicaid. Albany Times Union (Albany, NY) Retrieved from http://dialog.proquest.com/professional/docview/768176024?accountid=142257 on Dec. 12, 2016.*

(Continued)

*Primary Examiner* — Kito R Robinson
(74) *Attorney, Agent, or Firm* — Bookoff McAndrews, PLLC

(57) ABSTRACT

Provided is a computer-implemented system and method of preventing fraud. The system includes a communication unit for receiving a transmission of a prescription for durable medical equipment for a patient and data representing a biometric identifier of a health care provider. The communication unit receives a second transmission comprising notice of a claim by a durable medical equipment supplier for the prescribed durable medical equipment and a third transmission comprising verification that the patient received the durable medical equipment and data representing the biometric identifier of the health care provider. The system also includes a database for storing information and checking received information for instances of fraud.

19 Claims, 7 Drawing Sheets

(56) References Cited

U.S. PATENT DOCUMENTS

| | | | |
|---|---|---|---|
| 8,335,697 B2* | 12/2012 | Siegel | G06F 19/3456 705/2 |
| 8,818,824 B2* | 8/2014 | DeBusk | G06Q 30/00 705/2 |
| 2001/0050610 A1* | 12/2001 | Gelston | G06F 19/327 340/5.53 |
| 2002/0133376 A1* | 9/2002 | Fritschen | G06Q 10/10 705/2 |
| 2002/0169638 A1* | 11/2002 | Rodriguez-Cue | G06F 19/322 705/3 |
| 2002/0194131 A1* | 12/2002 | Dick | G06F 19/322 705/51 |
| 2003/0055687 A1 | 3/2003 | Rudy | |
| 2003/0083908 A1* | 5/2003 | Steinmann | G06Q 40/08 705/4 |
| 2003/0093298 A1* | 5/2003 | Hernandez | G06F 19/322 705/2 |
| 2003/0163350 A1 | 8/2003 | Rudowski et al. | |
| 2003/0171950 A1* | 9/2003 | Kilgannon | G06F 19/327 705/2 |
| 2003/0225627 A1* | 12/2003 | Mast | G06Q 30/0601 705/26.1 |
| 2003/0229519 A1* | 12/2003 | Eidex | G06F 19/328 705/2 |
| 2003/0233259 A1* | 12/2003 | Mistretta | G06Q 40/08 705/4 |
| 2004/0008123 A1* | 1/2004 | Carrender | G06K 19/07749 340/8.1 |
| 2004/0143454 A1* | 7/2004 | Kimmel | G06F 19/322 705/2 |
| 2005/0160052 A1* | 7/2005 | Schneider | G06Q 20/3674 705/67 |
| 2006/0010007 A1* | 1/2006 | Denman | G06F 19/321 705/2 |
| 2006/0098849 A1* | 5/2006 | Woodward | G06Q 20/206 382/124 |
| 2006/0132283 A1* | 6/2006 | Eberhart | A61B 5/117 340/5.2 |
| 2006/0190294 A1* | 8/2006 | Michelson | G06F 19/322 705/2 |
| 2006/0287882 A1 | 12/2006 | Hansel et al. | |
| 2007/0258626 A1* | 11/2007 | Reiner | A61B 5/411 382/115 |
| 2008/0059230 A1 | 3/2008 | Manning et al. | |
| 2008/0120136 A1 | 5/2008 | Barrett | |
| 2008/0133273 A1* | 6/2008 | Marshall | G06Q 10/10 705/3 |
| 2009/0125324 A1* | 5/2009 | Keravich | G06F 19/3462 705/2 |
| 2009/0157424 A1* | 6/2009 | Hans | G06Q 10/10 705/2 |
| 2009/0204433 A1* | 8/2009 | Darian | G06Q 50/22 705/3 |
| 2010/0057489 A1 | 3/2010 | Howe et al. | |
| 2010/0299158 A1* | 11/2010 | Siegel | G06F 19/3456 705/3 |
| 2011/0040983 A1* | 2/2011 | Grzymala-Busse | G06F 21/6245 713/189 |
| 2011/0077956 A1* | 3/2011 | Kapu | G06F 19/322 705/2 |
| 2011/0099087 A1* | 4/2011 | Reinhardt, Jr. | G06Q 10/087 705/26.81 |
| 2011/0105853 A1* | 5/2011 | Rakowski | G06Q 10/10 600/300 |
| 2012/0109829 A1* | 5/2012 | McNeal | G06Q 20/3674 705/67 |
| 2013/0006668 A1* | 1/2013 | Van Arkel | G06Q 10/10 705/3 |
| 2013/0124223 A1* | 5/2013 | Gregg | G06Q 30/0185 705/3 |
| 2013/0218599 A1* | 8/2013 | Highley | G06F 19/322 705/3 |
| 2014/0052466 A1* | 2/2014 | DeVille | G06F 19/328 705/2 |
| 2015/0012283 A1* | 1/2015 | Ryan | G06F 19/3437 705/2 |

OTHER PUBLICATIONS

Aston, G. (Jan. 25, 1999). HHS issues new fraud alert addressing home care. American Medical News Retrieved from http://dialog.proquest.com/professional/docview/768892439?accountid=142257 on Dec. 12, 2016.*

Thallner, K. (Oct. 11, 2006). Final anti-kickback safe harbors and stark exceptions for electronic prescribing and health records arrangements. Mondaq Business Briefing Retrieved from http://dialog.proquest.com/professional/docview/770982514?accountid=142257 on Dec. 12, 2016.*

D. Levinson, "CMS Response to Breaches and Medical Identity Theft", Office of Inspector General, Oct. 2012. https://oig.hhs.gov/oei/reports/oei-02-10-00040.asp.

C. Barrett, "Healthcare Providers May Violate HIPAA by Using Mobile Devices to Communicate with Patients", Federal Working Group, Oct. 2011, vol. 8, No. 2, Washington, DC, 5 pages. http://www.americanbar.org/newsletter/publications/aba_health_esource_home/aba_health_law_esource_1110_barrett.html.

M. Matthews, "Medicare and Medicaid Fraud is Costing Taxpayers Billions", Forbes, May 31, 2012. http://www.forbes.com/sites/merrillmatthews/2012/05/31/medicare-and-medicaid-fraud-is-costing-taxpayers-billions/.

C. Roehrenbeck, "Physician Identity Theft", American Medical Association, Oct. 2011, vol. 8, No. 2, Washington, DC, 5 pages. http://www.americanbar.org/content/newsletter/publications/aba_health_esource_home/aba_health_law_esource_1110_roehrenbeck.html-7k.

* cited by examiner

FIGURE 3

SYSTEMS AND METHODS FOR PREVENTING FRAUD

CLAIM TO PRIORITY

This application is a continuation-in-part of application Ser. No. 12/978,434, filed Dec. 24, 2010, now U.S. Pat. No. 8,311,857, the disclosure of which is incorporated herein by reference and to which priority is claimed.

FIELD OF THE INVENTION

The present invention is directed to systems and methods for fighting fraud, for example, systems for fighting fraud related to Medicare and Medicaid.

BACKGROUND

Medical fraud, specifically fraud related to Medicare and Medicaid, is prevalent in the United States, costing the government tens of billions of dollars a year. Though medical fraud is practiced on a wide scale, only a fraction of the criminals involved are ever apprehended, and out of those that are caught, only a fraction of the stolen money is ever recovered.

One major source of medical fraud is the use of deceased person's medical information to file false claims. This type of fraud has two major branches, one where the deceased is a patient and the other where the deceased is a medical physician. When a criminal impersonates a patient, the criminal typically files false claims relating to medical bills, such as doctor's visits and prescriptions, and is reimbursed by the government. When a criminal impersonates a physician or other healthcare provider, the criminal files false claims relating to services preformed. Currently, insufficient procedures and monitoring are in place to verify the information on these forms before payment is issued.

The government utilizes the Social Security Administration to keep track of deceased individuals in what is termed the Death Master File (DMF). Deaths, however, often go unreported, and absence of a person's name in the DMF is in no way an indication that a person is still alive. No law requires a death to be reported to the Social Security Administration, and family members of the deceased often do not know that deaths should be reported or do not understand the procedures required to do so, especially if the decedent was not of age to receive Social Security benefits. Even if a death is reported, it takes a long time to enter the DMF.

Another major source of medical fraud is related to the sale of durable medical equipment. Durable medical equipment may include items which are used to increase the quality of life of a patient, for example in the patient's home. Durable medical equipment is often covered by insurance companies, Medicare, and/or Medicaid. A supplier of durable medical equipment may provide goods to a patient and then receive reimbursement from an insurance company, Medicare, and/or Medicaid. Fraud may be introduced where a supplier submits multiple equipment reimbursements for a single patient or submits reimbursements for patients that do not exist. Suppliers may function as partially legitimate businesses or fake suppliers may be established by criminals to operate without ever actually providing goods or services to patients. Criminals may also fraudulently obtain DME and resell them on secondary markets.

A majority of the government's efforts to fight fraud are based on catching and prosecuting criminals after the fact. These efforts are both inefficient and ineffective at recovering money that is already stolen. By the time criminals are caught, the money is often hidden or spent. Thus, there remains a need to prevent such crimes before they occur.

SUMMARY

In accordance with an embodiment, provided is a computer-implemented system of preventing fraud. The system includes a communication unit for receiving a first transmission. The first transmission includes a prescription for durable medical equipment for a patient and data representing a biometric identifier of a health care provider. The communication unit receives a second transmission comprising notice of a claim by a durable medical equipment supplier for the prescribed durable medical equipment and a third transmission comprising verification that the patient received the durable medical equipment and data representing the biometric identifier of the health care provider. The system also includes a database for storing the first transmission.

In accordance with another embodiment, a computer-implemented system for preventing fraud includes a communication unit and a database. The communication unit receives a transmission comprising a prescription for durable medical equipment for a patient and data representing a biometric identifier of a health care provider. The database stores the prescription and the data representing a biometric identifier of the health care provider. The system is configured to analyze the prescription and the data representing a biometric identifier of the health care provider with previously stored data to prevent payment of a fraudulent claim for the durable medical equipment.

In accordance with a further embodiment is a method of preventing payment of a fraudulent claim. A transmission is received in a computer-implemented system including a database. The transmission includes a prescription for durable medical equipment for a patient and data representing a biometric identifier of a health care provider. The prescription and the data representing the biometric identifier is stored in the database. The data representing the biometric identifier of the health care provider is compared with preexisting biometric identifier data stored in the database to authenticate the data representing the biometric identifier of the health care provider. Notice of a claim is received for the prescribed durable medical equipment. Verification is received that the patient has received the prescribed durable medical equipment. The verification includes data representing a biometric identifier of the health care provider. Authorization to pay the claim is transmitted.

BRIEF DESCRIPTION OF THE DRAWINGS

FIG. 3 is an exemplary death notice form.

DETAILED DESCRIPTION OF EXEMPLARY EMBODIMENT(S) AND EXEMPLARY METHOD(S)

Figure 1:
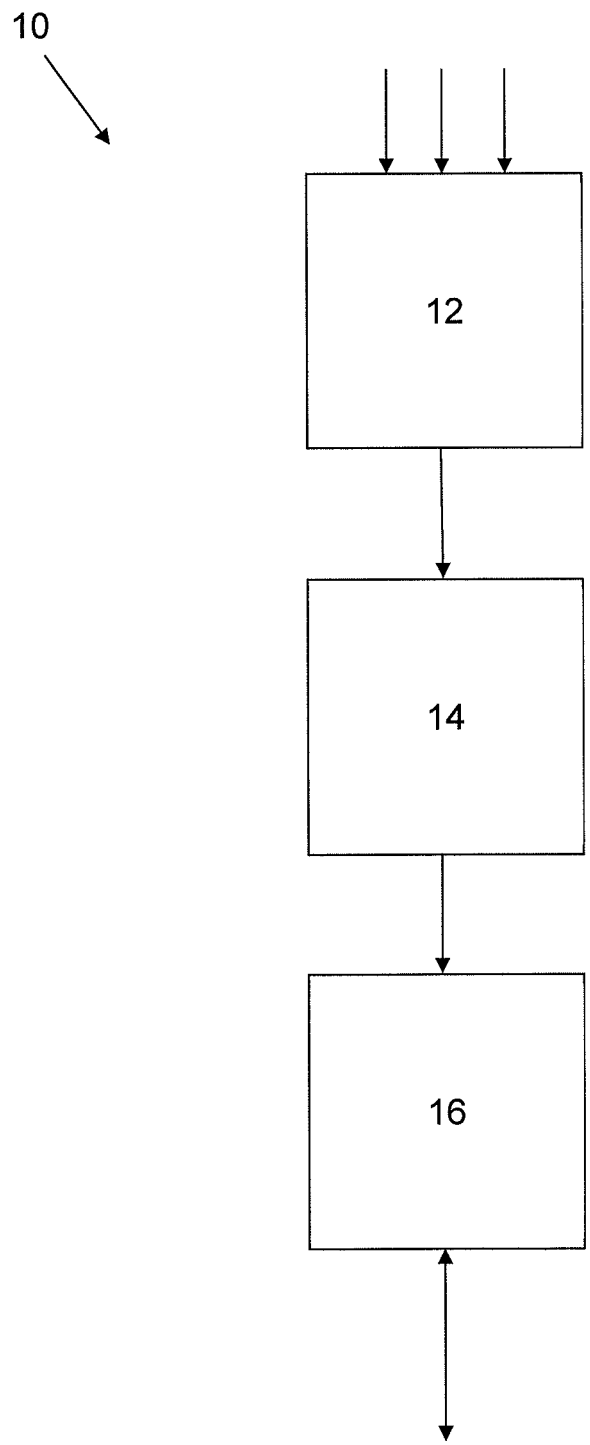
FIG. 1 is a flowchart overview of an exemplary death index system.

Reference will now be made in detail to exemplary embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in connection with the exemplary embodiments and methods.

Exemplary embodiments are directed to systems and methods of preventing fraud related to Medicare and Medicaid billing. These programs are handled by the Centers for Medicare and Medicaid Services (CMS), a component of the Department of Health and Human Services (HHS). In the interest of brevity, Medicare and Medicaid will be hereinafter referred to as MS. It should be understood, however, that the systems and methods described herein may be adopted by or applied to private health care and life insurance companies.

In an exemplary embodiment, the systems and methods operate to prevent fraud based on the use of a decedent's personal information, especially information that is unique to a specific individual, such as a Social Security Number (SSN). The system can prevent the fraudulent use of a deceased patient's information and the medical identification of a deceased health care provider.

In an exemplary embodiment shown in FIG. 1, a system generally designated by reference numeral 10 comprises a computer system, software system, internet based applications, a network of computer systems, such as a cloud computing network, or any combination thereof. The system 10 will be described in general terms, without in depth discussion of specific hardware and software components that may be incorporated into the system 10. One of ordinary skill in the art will recognize that there are many possible computer system designs suitable for use with these exemplary embodiments, and that various additions or modifications of such systems may be made.

The exemplary system 10 of FIG. 1 includes an information receiving unit 12. The information receiving unit 12 is designed to receive information from a variety of outside sources, the examples of which are described below. The information receiving unit 12 may receive information electronically, for example through an electronic document, form, or other file. The information may be submitted by email, web form, or other electronic transfer. Alternatively, the information may be entered locally using an input or storage device, such as a keyboard, mouse, compact disc, hard disk, or flash drive. The information receiving unit 12 may actively and/or passively obtain information from an outside source. As such, the information receiving unit 12 may be designed not only to receive information but to search, analyze, compile, and alter information.

The information receiving unit 12 is in communication with a central database 14 for forming a death index. The database 14 may be a centralized server or a network of devices, though any known procedure for storing and indexing data may be used. The database 14 may store information received or it may process the information and pass on specific communications to an outside source without storing it. The system 10 may contain appropriate software and hardware for analyzing, organizing, and otherwise manipulating and transmitting the records in the database 14.

The system 10 further includes a communication unit 16 for retrieving information from the database 14 and transmitting the information to a variety of sources. The communication unit 16 may include a communications interface for communicating with these sources in any known fashion, such as a direct electronic connection, a direct network connection, a LAN connection, modem connection, etc. The communications unit 16 may also be designed to interact with or manipulate outside systems, as will be discussed in further detail below. It should be noted that information receiving unit 12, the database 14, and the communication unit 16 are discussed as individual components for the sake of clarity. These units, however, may be the part of a single unit or any combination of units.

Figure 2:
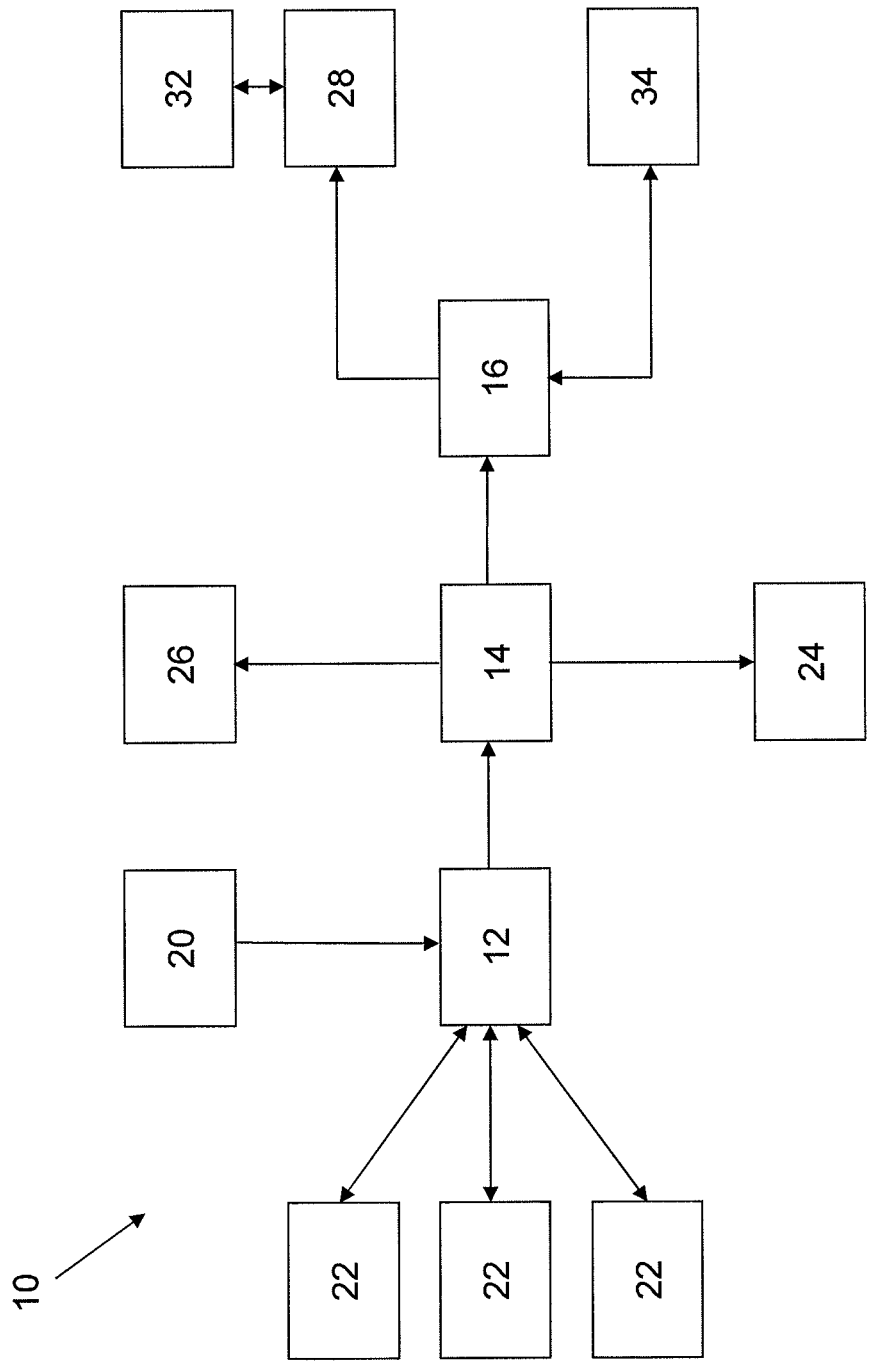
FIG. 2 is a flowchart of an exemplary death index system.

As best shown in FIG. 2, the system 10 may receive information from a variety of sources. For example, the information receiving unit 12 may receive information from a form 20 filled out by one or more individuals. The form 20 may be filled out and submitted electronically by an individual. In an exemplary embodiment, software containing one or more types of forms 20 is provided and can be installed at individual locations. The form 20 may additionally be a web form which is filled out and submitted electronically by an individual on a website. In an alternative embodiment, the form 20 may be filled out, either by hand or electronically, and then physically submitted to a central location. The form 20 may then be entered into the database 14 either manually or through the use of an optical scanner or image recognition program.

Figure 3:
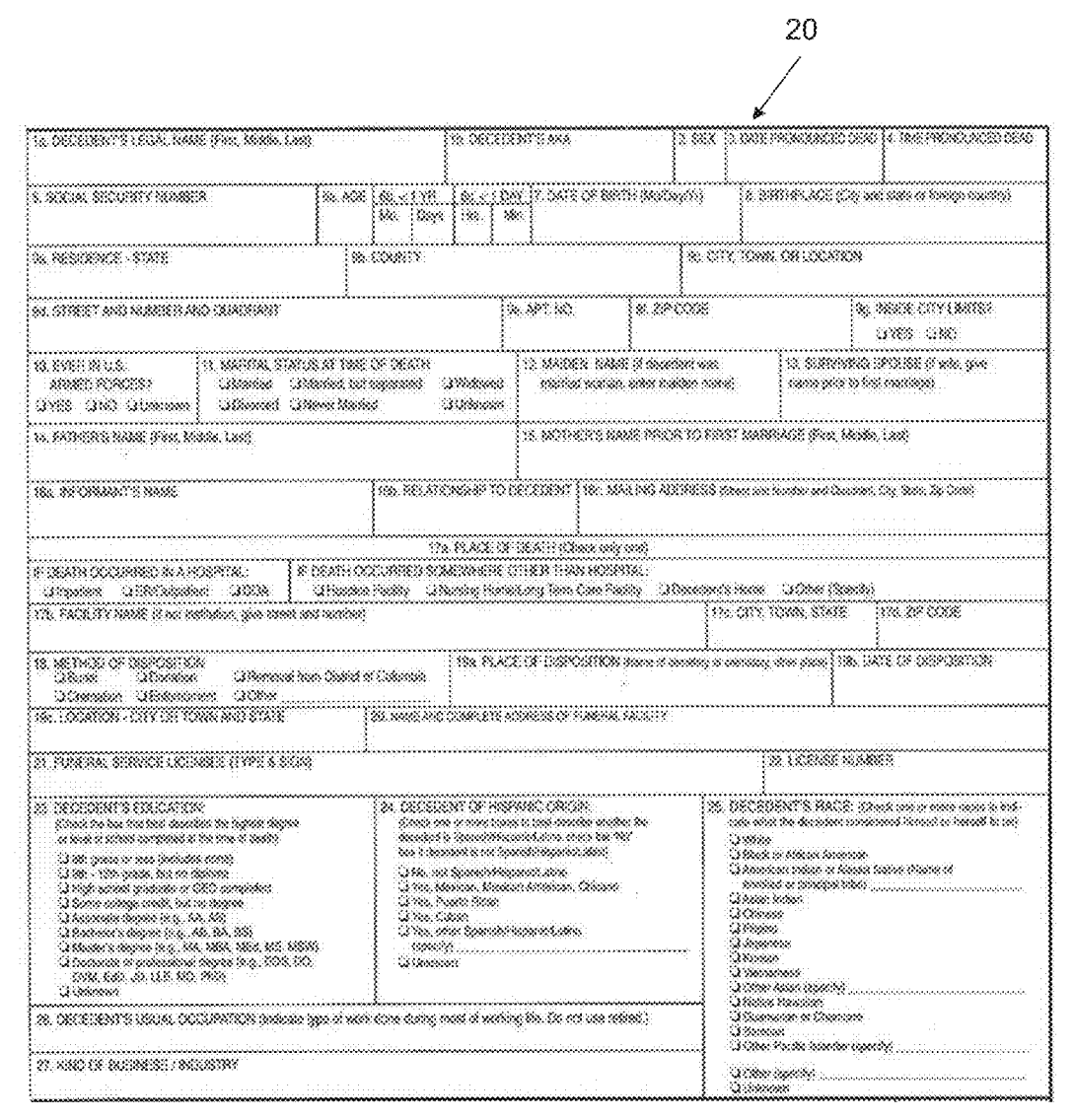

FIG. 3 shows an exemplary form 20. The form 20 has a number of categories relating to personal information of the deceased, such as name, sex, SSN, age, residence, birth date, address, etc. Alternative forms may be used, and the categories may vary from those found in the form 20 shown in FIG. 3. For example, the form 20 may provide additional fields representing a medical identification number, insurance identification number, and, in the case where the decedent is a health care provider, a physician identification number. The form 20 provides more information than is typically stored in death databases, for instance, the DMF. The more detailed form 20 allows for greater accuracy in the death index database 14. In an exemplary embodiment, the form 20 either includes or is accompanied by a picture of the deceased individual. The submitted picture may the most recent photo of the deceased prior to death and/or a photo of the deceased after death. This information is used to prevent fraudulent claims, as discussed in greater detail below.

Upon receipt by the information receiving unit 12, the form 20 is checked for completeness. This check may be performed by the information receiving unit 12 or by another component of the system 10. If the form 20 is incomplete, an error message or other notification may be sent to the source of the form 20 by the communication unit 16. The form 20 may indicate that all known information has been submitted, either on an initial or secondary submission, and be entered into the database 14 as is.

The form 20 may be completed by a funeral director, a relative, a government official, a medical examiner, or other qualified individual. In various exemplary embodiments, funeral directors are the sole source of information for updating the database 14. Designating a funeral director as the outside source for submission of the form 20 is particularly useful because funeral directors are involved in some capacity in almost all deaths occurring in the United States. Other sources, such as newspaper obituaries, are not reliable because they do not always contain every death, and even then the information is incomplete and subject to error. Family members, if there are any, are often in a state of grief, and cannot be relied upon to submit information. Government officials are not always in the position to be notified of every death, and may not know complete information about the individual. A funeral director, however, must be involved with the disposal of a body, be it through cremation or burial, for almost every death in the country. Additionally, funeral directors often have close personal contact with family members, making them available to find out information on the decedent. By utilizing funeral directors, the database 14 can obtain the most accurate and up-to-date information as quickly as possible.

Funeral directors may be motivated to provide submissions to the database 14 for a variety of reasons. They can be offered financial incentives or include a fee for preparing the submission as a service charge, either in addition to or as a part of a predetermined package. Additionally, funeral directors may be motivated to provide submissions in order to comply with the Red Flags Rule. The Red Flags Rule was implemented by the Federal Trade Commission and requires many businesses and organizations to create and implement a written identity theft prevention program designed to detect the warning signs, or "red flags," of identity theft in day-to-day operations. The Red Flags Rule requires businesses to develop a four step procedure which: 1) identifies possible sources of identity theft that may arise in their everyday business practices; 2) takes steps to detect the identity theft established in Step 1; 3) sets forth actions that will be taken when identity theft is detected; and 4) addresses how the program will be reevaluated and updated on a regular basis. By submitting information to the present system 10, funeral directors can easily satisfy all the requirements of the Red Flags Rule.

In addition to the form 20, the information receiving unit 12 may acquire information from external databases 22 to be used as a secondary source of information. The external databases 22 may include the DMF, the Center for Disease Control National Death Index, and vital records maintained by states. The information receiving unit 12 may acquire information from the external databases 22 automatically, for example by searching online, or the information may be obtained through manual searching and entered into the information receiving unit 12. The external databases 22 should be searched on a periodic basis. In an exemplary embodiment, the system 10 has a relationship with one or more external databases 22, so that whenever an external database 22 is updated, a signal or communication is sent to the information receiving unit 12 providing the new data. It should be understood that while forms 20 and databases 22 are discussed herein and shown in FIG. 2 as potential outside sources, the system 10 may contain additional or alternative outside sources.

Upon receipt of information, the information receiving unit 12 creates a record and submits it to the database 14. The information receiving unit 12 may also format the received information in a predetermined manner, so that the information can be quickly and efficiently compiled by the database 14. For example, the information receiving unit 12 may read the information supplied to it, and convert all the information into binary format to be stored in memory by the database 14.

Upon receiving a submission, the database 14 checks for conflicting or repetitive information. Repetitive information may represent information received from an external database 22 that was already submitted by a form 20. If repetitive information is found, it is ignored and not reentered into the database 14. Conflicting information may represent a new entry that shares some of the same personal information with and older entry. If conflicting information is found, an alert unit 24 creates an alert which is reviewed by an administrator. Conflicting information may commonly appear in relation to the decedent's name. This represents little or no concern in preventing fraud; however this information may still be flagged and checked by an administrator for the sake of thoroughness. Conflicting information relating to personal information that is unique to the individual, such as a decedent's SSN, medical identification number, insurance identification number, and, in the case where the decedent is a health care provider, a physician identification number, may represents a serious fraud threat, and should be checked by an administrator. In an exemplary embodiment, the alert unit 24 is capable of creating at least two distinct types of alerts. The first type of alert represents low priority conflicting information, such as a person's name, while the second type of alert represents high priority conflicting information, such as a conflicting SSN. In an exemplary embodiment, an administrator is able to access the system 10 remotely, such as through a personal computer or smart phone, which connects to the system 10, through a network or through virtualization software. The alerts are preferably stored in the system 10 by the alert unit 24 until cleared by an administrator.

After the data has been converted and passes any conflict checks, the database 14 may perform a variety of operations. For example, the database 14 may store the record created by the information receiving unit 12 in a memory unit 26. The memory unit 26 may consist of a single centralized server or a network of devices. Various components which make up the memory unit 26, including different hardware and software components, will be understood by one of ordinary skill in the art.

After the database 14 is updated, the communication unit 16 may retrieve the records from the database 14. In an exemplary embodiment, the communications unit 16 provides an output to a billing system 28. This billing system 28 may be associated with MS billing operations, with a doctor's office, or with other health care provider billing operations. Typically, the CMS contracts with a private company to handle claim billings. The contractors may also be in charge of investigating fraud, thus encouraging them to utilize or communicate with the present system 10. In an exemplary embodiment, the database 14 is able to receive information about a deceased person and communicate this information directly to a billing system 28 through communication unit 16. As shown in FIG. 3, part of the information received by the database 14 relates to the decedent's occupation. In an exemplary embodiment, when this information is received by the database 14, it checks to see if the decedent's occupation was a physician or other health care provider. If so, the communication unit 16 sends this information to the billing system 28. This communication also prevents billing for services performed by the deceased physician. The communication may take place through a suitable telecommunication system, such as an electronic, optical, or satellite communication system. In an exemplary embodiment, the system 10 automatically prevents the entering of billing information related to a deceased person. This may be accomplished directly by the system 10 or by the billing system 28 as a result of the communication, as discussed in greater detail below.

Figure 4:
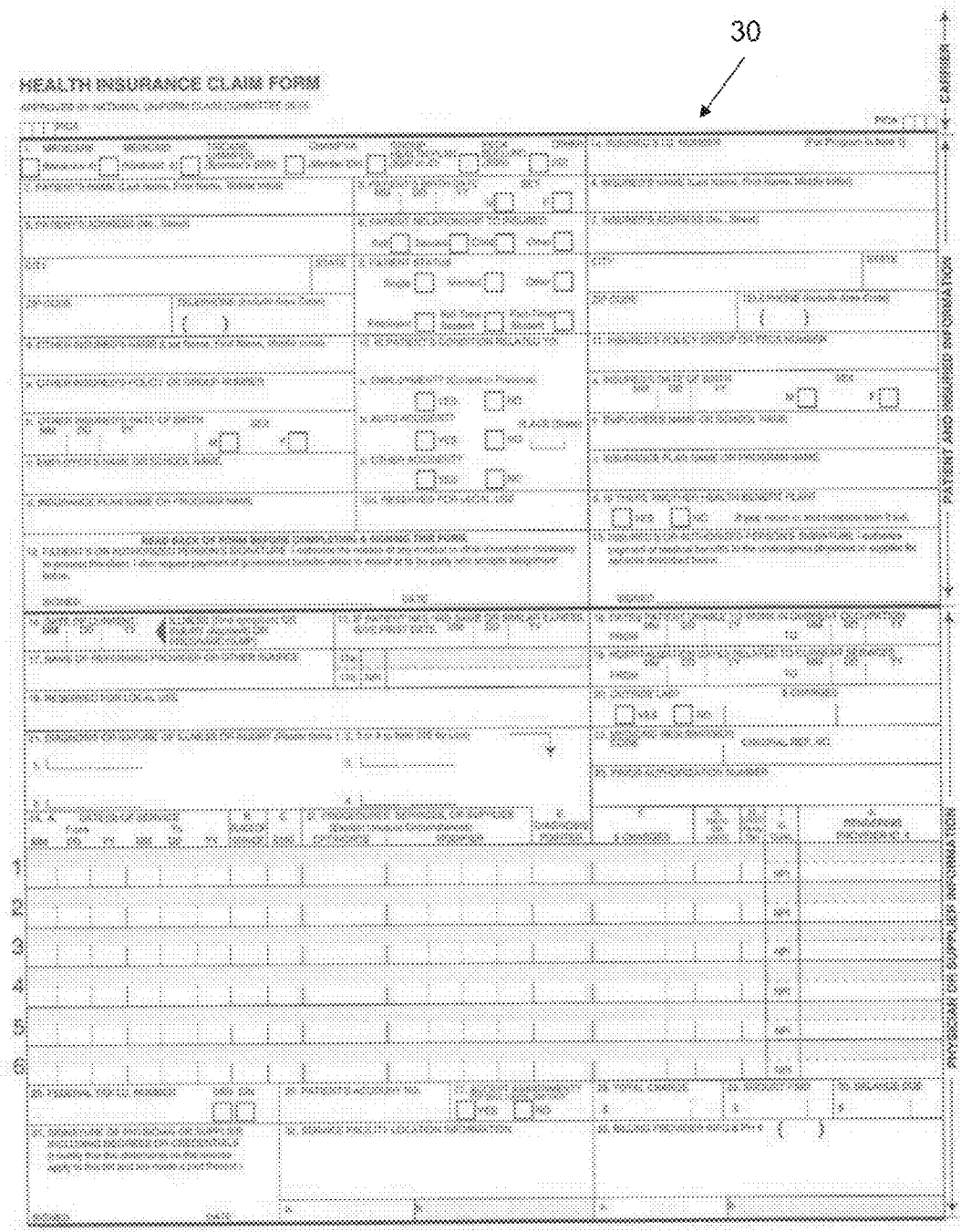
FIG. 4 is an exemplary billing form.
Figure 5:
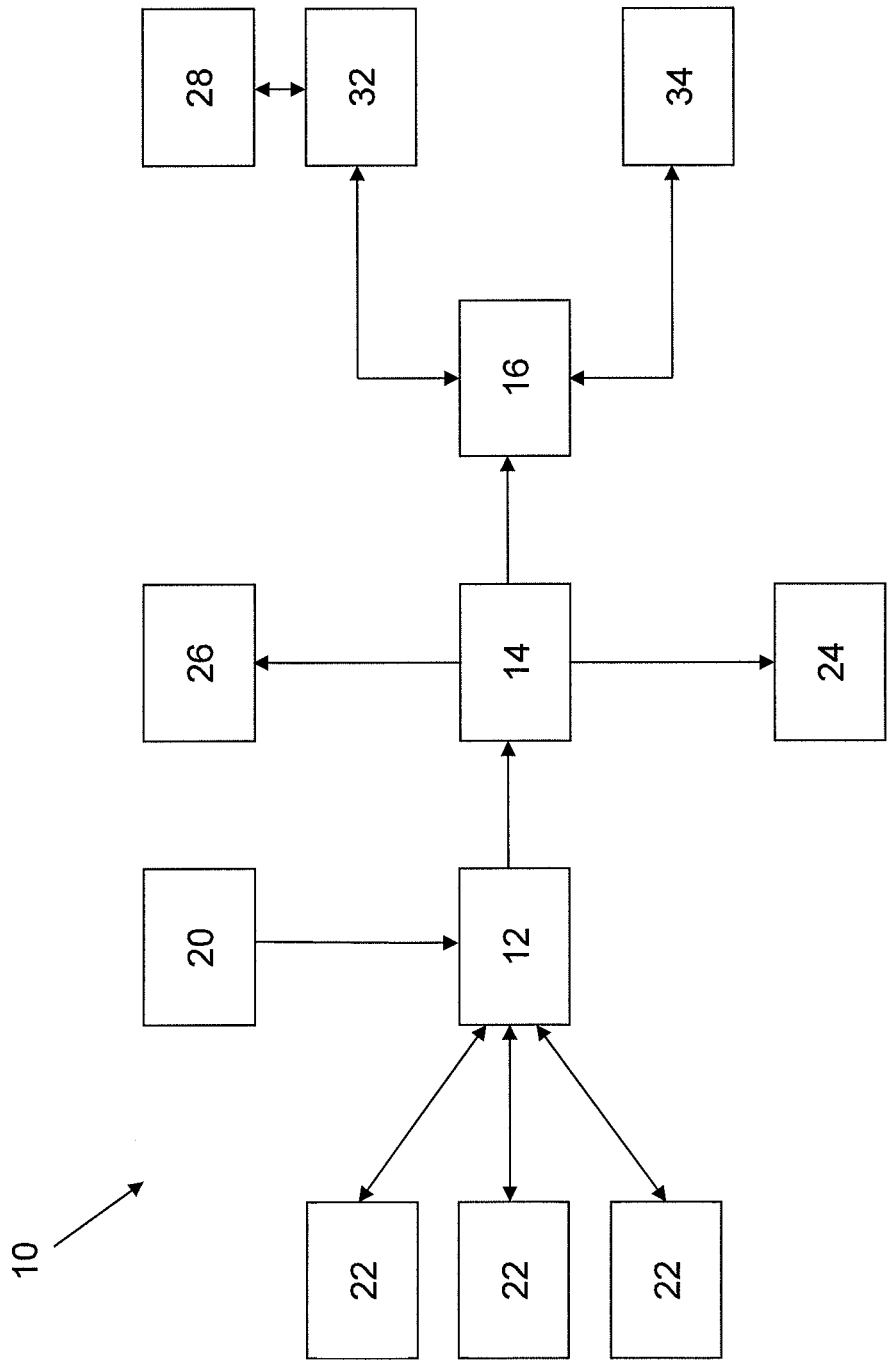
FIG. 5 is a flowchart of an exemplary death index system.

FIG. 4 shows an exemplary medical billing form 30. Preventing a deceased person's billing information may be done by blacking out, fading, or otherwise making it impossible to enter information into the billing form 30 when it is determined that a decedent's social security number, patient id number, or other type of identification number is being used. In an exemplary embodiment, the communication unit 16 sends a communication to a billing system 28 indicating that a person is deceased. The billing system 28 then stores this information. An analyzing unit 32 then analyzes or otherwise monitors information stored in the billing system 28 or entered into a billing form 30. As shown in FIG. 5, alternatively, or in addition to monitoring by the billing system 28, the communication unit 16 communicates directly with the analyzing unit 32, which monitors the billing system 28.

The analyzing unit 32 may utilize keystroke recognition and logging, as well as or in addition to form monitoring to analyze information input to the billing form 30. Known techniques, such as utilizing scripting or program languages, for example Javascript, can be used by the analyzing unit 32 to implement scanning and monitoring of the billing form 30. The billing form 30 may be present in a machine readable electronic format, for example having extensible markup language (XML), such as an Xform, or interactive PDF. The billing form 30 may also be present in a web-based application having hyper text markup language. These types of documents typically have tags associated with specific fields. The analyzing unit 32 monitors the individual tagged fields by scanning the source code of the billing form 30. The information present or entered into each field is then compared with the information received from the communication unit 16 or information that is present in the database 14. For example, the analyzing unit 32 monitors a field tagged as containing a SSN, insurance number, or other patient identification number. As shown in FIG. 4, the second part of the billing form 30 addresses physician or supplier information. As with the patient information, the system may monitor information submitted on this section of the billing form 30 and determine if a deceased physician's identity is being used.

In addition to monitoring the information as it is being entered, the analyzing unit 32 may decode and determine the content of the field after the information has been completely entered. This may be accomplished either upon submission of the entire billing form 30 or upon the determination that a field has been completed. The analyzing unit 32 may conclude that a particular field has been completed by determining information is being entered into a different field or by determining the position of a text entry cursor. Additionally, the electronic form may have field information which indicates that a specific number of characters should be entered into the field. The analyzing unit 32 may determine when this number is reached and begin comparing the information inputted to the billing form 30 with the information retrieved from the database 14.

The analyzing unit 32 may analyze every field, or it may be designed to analyze certain fields identified by specific tags. For example, certain fields, such as a patient or health care provider's identification number, are given a higher weight or priority. If only a part of the billing form 30 is being actively monitored, and information relating to a deceased person is found in these fields, a complete check of the billing form 30 may then be performed either manually or by the system.

The analyzing unit 32 may also analyze forms not in an XML format. For example, if a hardcopy of the billing form 30 is submitted, the analyzing unit 32 may scan the form to analyze the information, such as through optical character recognition. Forms may also be present on electronic paper and input provided via an electronic stylus. This information may be received by the billing system 28 and decoded by the analyzing unit 32. Other electronic and non-electronic forms that are known in the art can be analyzed by the analyzing unit 32 using an appropriate method as will be understood by those of ordinary skill in the art.

As discussed above, various exemplary embodiments incorporate the submission of a photograph to the information receiving unit 12. Though the billing form 30 does not require a photograph, the submission of such could be mandated for both a patient and a physician. The analyzing unit 32 may then analyze the photograph, for example, by using image recognition, to compare the picture accompanying the billing form 30 with those present in the database 14. This may be done as a secondary check, when some conflicting information is found, or it may be done for all submissions.

If the analyzing unit 32 determines that information of a deceased person has been entered, the billing form 30 is flagged and payment of the bill is prevented. The billing system 28 or contractor is also notified of the presence of fraudulent information. Payment may be prevented in a variety of manners, such as preventing information from being entered into the billing form 30, preventing the submission of the billing form 30, or by interacting with the billing system 28 to prevent the acceptance of the billing form 30. It should be understood that preventing payment may depend in part on the make up of the billing system 28. Accordingly, various procedures and the components for implementing payment prevention will be understood by those of ordinary skill in the art upon viewing the disclosure setforth herein.

In addition to preventing payment, the analyzing unit 32 may send an alert to any individual designated by the billing system 28. An alert may also be sent to an administrator of the system 10 so that a follow up may be made to determine the notice was received and heeded. In an exemplary embodiment, an alert may also be sent to authorities to inform them of potential fraud. Either the system 10 or the billing system 28 may capable of tracking the location of submissions and provide data on the submitting entity along with the alert of fraud and evidence of the fraudulent information to the authorities.

In an exemplary embodiment, the communication unit 16 may have a secondary output 34. This output may inform other entities of an individual's death. These entities may include one or more financial institutions, such as banks, credit cards, lending institutions, trusts, etc. Additionally, the family of the decedent may specify entities they wish to have notified. This may be done either through the funeral director, who can submits such data with the death information, or family members may directly access the system 10 to input this information. The system 10 may also be capable of receiving a request for information from outside entities.

Figure 6:
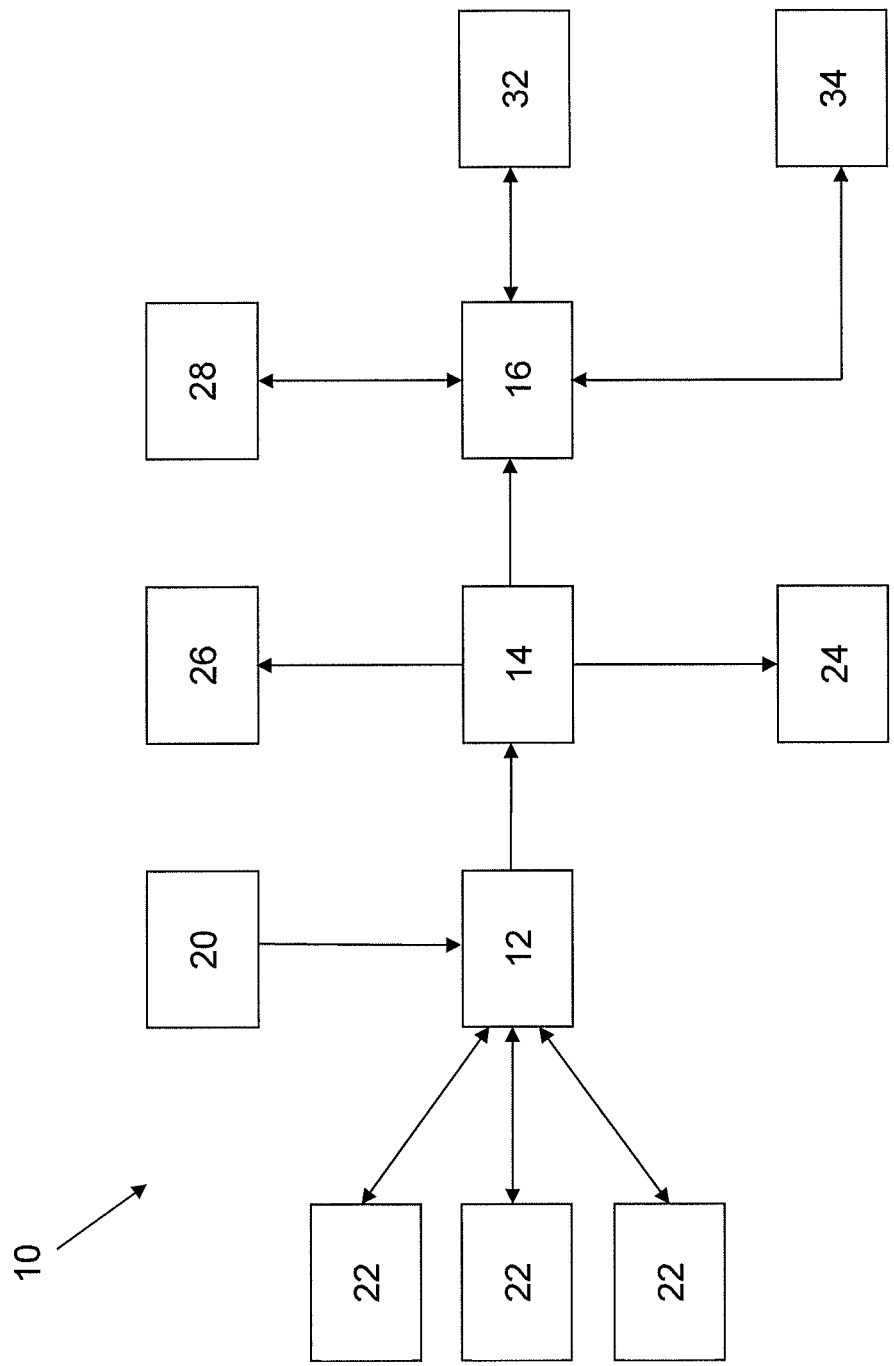
FIG. 6 is a flowchart of an exemplary death index system.

FIG. 6 shows an exemplary embodiment where the billing system 28 initiates communication with the system. Before paying a submitted bill 30, the billing system 28 sends a communication to the communication unit 16. This communication includes the information submitted in the billing form 30. The information is analyzed by the analyzing unit 32 as discussed above. The analyzing unit determines if either the patient or the health care provider is deceased. If there is no fraudulent information present in the billing form 30, the analyzing unit 32 determines it is ok to pay the bill, and the communication unit 16 sends a signal back to the billing system 28. If the analyzing unit 32 determines that a deceased individuals information is being used, it instructs the communication unit 16 to send an alert to the billing system 28 indicating the presence of fraud and preventing payment of the bill 30.

While the billing system 28 has been described as an external entity, various exemplary embodiments may include the billing system 28 within the present system 10 as a single inclusive system. Additionally, while an exemplary computer system has been discussed, various exemplary embodiments are contemplated which comprise software containing instructions stored thereon which, when executed by a computer, cause the computer to perform some or all of the functions and tasks described above. The above described exemplary systems and processes are designed to fight fraud related to medical billing by utilizing real-time blocking of fraudulent claim forms. The system 10 may be completely automated and instantly update after receiving the notice of a death. This provides a great advantage over other databases, such as those run by government entities, which update periodically, such as every year or 15 months, because any amount of elapsed time provides criminals with an opportunity to steal greater sums of money.

Figure 7:
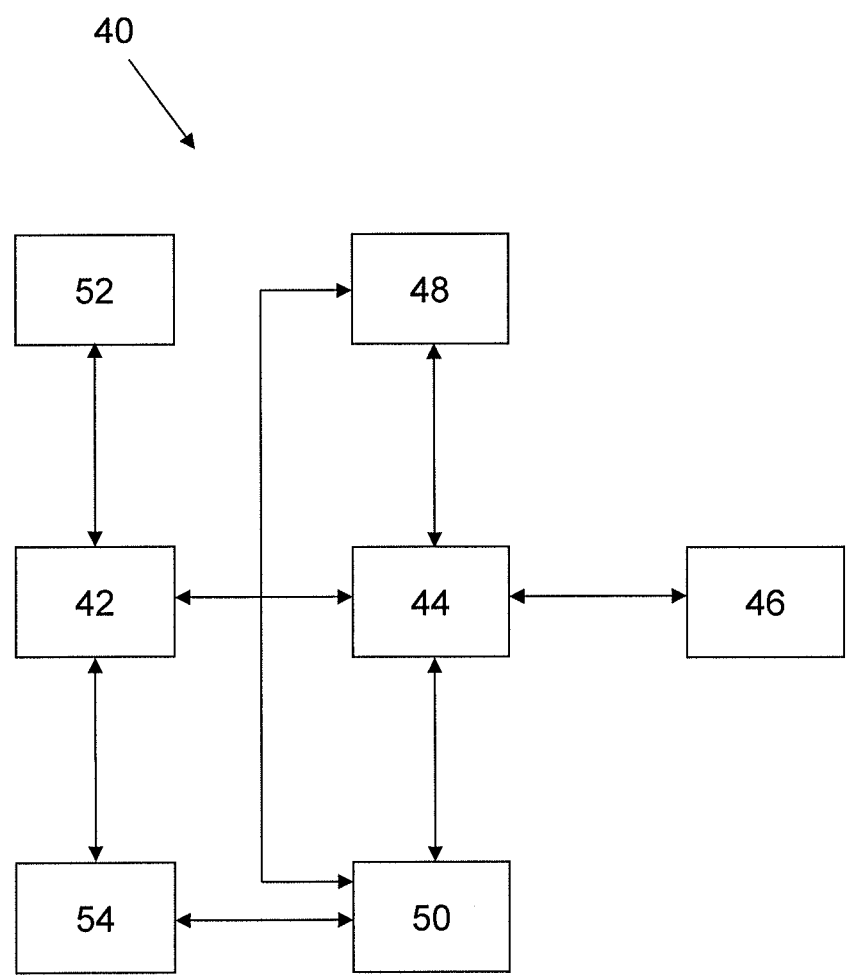
FIG. 7 is a flowchart of an exemplary system for preventing fraud in DME billing.

As depicted in FIG. 7, an exemplary embodiment of a system 40 may prevent fraudulent claims related to durable medical equipment (DME). While a separate system 40 is shown in FIG. 7 and described below, the systems shown in FIGS. 2, 5, and 6 and discussed above may be adapted to perform the functions described below and vice versa. In order to obtain durable medical equipment a patient needs authorization such as a prescription, which may also be referred to as a Certificate of Medical Necessity (CMN), completed by a health care provider 42, for example a physician. CMN will be used herein for brevity, but may encompass any form of prescription, authorization, or order provided by a health care provider 42 for DME. Criminals may utilize stolen or duplicate CMNs to receive fraudulent reimbursements for durable medical equipment. Criminals may also utilize identities of deceased physicians to complete fraudulent CMNs. In various exemplary embodiments, the system 40 includes a communication unit 44 for receiving an initial submission of a CMN, for example an electronic CMN submitted by a health care provider 42. The communication unit 44 facilitates the receipt and transmission of information between the system 40, and users thereof. The communication unit 44 may receive, compile, and/or transmit data. The communication unit 44 may include various software and hardware components as would be understood by one of ordinary skill in the art. For example, the communication unit 44 may include a computing device connected to a network and be configured to transmit and receive electronic communications and other electronic data between various users and the system 40. The communication unit 44 may include a web interface, portal, web server, or other networking features. Though described as a single unit here for simplicity, the communication unit 44 may act similar to a combination of the information receiving unit 12 and communication unit 16 described above, or alternatively the communication unit 44 may be replaced by the information receiving unit 12 and communication unit 16 discussed above. The different units described herein may be single distinct components or may be a single component which performs multiple functions as would be understood by one of ordinary skill in the art.

The CMN may be submitted through an electronic communication, for example an email, email attachment, or an electronic-fax. The CMN may also be submitted over the Internet through an appropriately designed web interface. The CMN may also be mailed or faxed to a location and entered manually into the system, for example by scanning. Upon receipt of the CMN, the form may be checked for completeness. If the CMN is incomplete, an error message or other notification may be sent to the submitting health care provider 42. After receipt, the CMN may be stored in a central database 46. The initial submission of the CMN may also be submitted by a health care provider 42 to a billing contractor 48, referred to herein as any person, group, or system performing a billing operation, for example an insurance company or a CMS billing contractor, and/or to one or more DME suppliers 50. The initial submission of the CMN may inform a billing contractor 48 and/or DME supplier 50 of a legitimate DME order. Localizing the initial CMN submission to the database 46 and providing access to the database 46, for example through the communication unit 44, to billing contractors 48 and/or DME suppliers 50 may centralize and simplify the process.

The initial CMN submission may be accompanied by one or more identifiers authenticating the health care provider 42. For example the initial CMN submission may be accompanied by a PIN or National Provider Identification (NPI) number associated with the health care provider. 42. The NPI, however, may not be secure as they are publicly available and may be obtained by criminals. In various exemplary embodiments, the initial CMN submission is accompanied by a biometric identifier unique to the health care provider 42. The system 40 is configured to determine the legitimacy or authenticity of the biometric identifier, for example by comparing the data associated with the biometric identifier with data stored in the database. The biometric identifier may come from a biometric scanner 52. The biometric scanner 52 may include one or more fingerprint scanners and/or a retinal scanner, though other biometric scanners may also be used. For example, the health care provider 42 may be provided with a fingerprint scanner and may have to include data from the fingerprint scanner with each CMN submission. The biometric scanner 52 may be a stand-alone device or it may be incorporated into another electronic device such as a mobile phone, tablet, laptop, or computer. For example, LG makes a retinal scanner, the IrisAccess 2200, and certain smartphones, such as the Motorola Atrix, include a fingerprint scanner. Another example is the DigitalPersona U.are.U® 4500 Fingerprint Reader which can connect to a computer, laptop, or other electronic device through a USB connection. Software may be provided to the health care provider 42 on a computer, laptop, tablet, phone, or other electronic device which provides an interface for filling out the CMN and integrates the submission of the CMN with the biometric identifier data.

After the initial CMN submission, a patient 54 may pick up the required DME from the DME supplier 50. The DME supplier 50 may then submit a claim for the supplied DME for payment. The claim may be submitted directly to the billing contractor 48, or it may be submitted through the system 40, for example via the communication unit 44. Upon receipt in the system 40, the claim may be stored in the database 46. In various exemplary embodiments, a billing contractor 48 will require additional authorization or verification before release of a payment. This additional authorization may confirm that the patient actually received the DME. In various exemplary embodiments, the health care provider 42 checks with the patient 54 after they receive the DME to make sure that it was provided properly and that the patient 54 is using the DME. The health care provider's verification may be accomplished by direct communication with the patient 54 or by communication through the system 40, for example via the communication unit 44. Authorization may then be sent to the billing contractor 48 to release the funds to the DME supplier 50. The communication to release the funds may be accomplished by direct communication between the health care provider 42 and the billing contractor 48, or by communication through the system 40, for example via the communication unit 44. If an instance of fraud is suspected or detected, the system 40 may prevent payment of the claim, for example by notifying the billing contractor 48. The system may include a separate billing unit which is capable of analyzing claims and/or a separate notification unit (not shown). Notification may also be provided through the communication unit 44. In various exemplary embodiments, the verfication may include a second biometric identifier provided by the health care provider 42. The second biometric identifier may be the same as the first biometric identifier and may include one or more fingerprint scans or a retinal scan from a biometric scanner 52 as discussed above. After the final verification is provided, authorization may be sent to the billing contractor 48 to release the funds to the DME supplier 50.

In various exemplary embodiments, each action from the initial CMN submission through the final payment may be stored in the database 46. Each action may be stored individually and/or stored together as part of a single transaction file. The system 40, for example the database 46 or a separate billing unit (not shown) may cross-check new transactions with old transactions. Various algorithms may be used to check for fraud in each new transaction. The name of the patient 54 and the type of DME may be checked with existing transactions to see if a patient 54 is attempting to fraudulently obtain DME from different health care providers 42 and/or DME suppliers 50. The system 40 may also check to determine if a certain piece of DME is being order within a standard time frame for re-order. The name, address, or other personal information of a patient 54 as well as the health care provider 42 may also be compared with past transactions for incidences of fraud, such as multiple similar transactions. A new transaction may also be checked to see if a DME supplier 50 is submitting multiple copies of the same CMN or is attempting to submit a CMN that has already been submitted elsewhere. Various algorithms may also be used to analyze a batch of transactions for fraud. For example, the number of CMNs submitted by a health care physician or a DME supplier over a set period of time (day, week, month, year, etc.) may be compared with a statistically calculated maximum number of patients 54 that can be seen by a health care provider 42 or served by at DME supplier 50. For example, the maximum number of patients 54 that can be seen by a health care provider 42 may be based on, but not limited to, the health care provider's type of practice, size of the practice or office, surrounding area population, and past numbers. The maximum number of patients 54 that can be served by a DME supplier 54 may be based on, but not limited to, the type of supplies, the size of the DME's suppliers facilities (including sales offices and storage), the size of the population in the surrounding area, and past sales numbers. If the possibility of fraud is detected, the system 40 may flag the transaction and/or send an alert to authorities, the health care provider 42, the billing contractor 48, and/or the DME supplier 50.

Various exemplary embodiments are related to a method of preventing fraud in DME orders. A health care provider 42 submits a CMN and a personal identifier such as a NPI number or data representing a biometric identifier. The CMN and the personal identifier is received by the communication unit 44. The CMN and personal information may be stored in a database 46. A CMS billing contractor 48 and/or a DME supplier may be notified of the submitted CMN directly from the health care provider 42 or through a notification transmitted by the communication unit 44. A patient 54 may then obtain the prescribed DME from the DME supplier 50. After the patient 54 obtains the DME from the DME supplier 50, the health care provider 42 may check with the patient 54. If the health care provider 42 believes a fraudulent transaction has not taken place, the health care provider 42 will then provide confirmation to the billing contractor 48, either directly or through the system 40. After confirmation has been received by the billing contract 48, funds may be released to the DME supplier 50.

In various exemplary embodiments, the system 40 for detecting fraud related to DME billing may be combined with the death index system 10. The combined system may include a database for obtaining death information as discussed in the various exemplary embodiments above and depicted in FIGS. 2, 5, and 6. The combined system may also be configured to receive CMNs related to DME and act to verify DME billing submissions as discussed above and depicted in FIG. 7. These systems 10, 40 may also remain separate and be configured to communicate with one another, for example via communication units 16, 44, or through a separate, dedicated communication unit.

In various exemplary embodiments, the communication unit 44 of the system 40 depicted in FIG. 7 may receive information relating to deceased individuals as discussed herein. This information may then be stored in the database 46. After an initial submission of a CMN, the system may check to determine if the health care provider 42 who submitted the CMN is deceased. If the health care provider 42 is determined to be deceased, the system may flag the transaction as well as send an alert to authorities, the billing contractor 48, and/or the DME supplier 50.

Health care providers 42, billing contractors 48, DME suppliers 50, and others may be motivated to utilize the system 40 described above for a variety of reasons. They can be offered financial incentives or include a fee for preparing the submission as a service charge, either in addition to or as a part of a predetermined package. Additionally, they may be motivated in order to comply with the Red Flags Rule discussed above, as well as the Health Insurance Portability and Accountability Act (HIPPA) and the related security rules outlined by the department of Health and Human Services. The HIPPA security rules outline national standards designed to protect individuals' electronic Protected Health Information and the transfer and submission of such information by people in the health industry.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. For example, the DME sytem 40 may be utilized with other insurance claims, such as pharmaceuticals. Additional embodiments are possible and are intended to be encompassed within this specification and the scope of the appended claims. The specification describes specific examples to accomplish a more general goal that may be accomplished in another way.

Only those claims which use the words "means for" are to be interpreted under 35 U.S.C. 112, sixth paragraph.

What is claimed:

1. A computer-implemented system for preventing submission and payment of fraudulent claims comprising:
   an electronic device used by a health care provider, the electronic device including a biometric scanner;
   a communication unit for receiving:
   a first transmission prepared and transmitted by the electronic device comprising a prescription for durable medical equipment for a patient prepared by the electronic device and first data representing a biometric identifier of the health care provider generated by the biometric scanner of the electronic device, the first data representing the biometric identifier being generated to be uniquely included in the first transmission, a second transmission comprising notice of a claim by a durable medical equipment supplier for the prescribed durable medical equipment, and a third transmission prepared and transmitted by the electronic device comprising verification that the patient received the durable medical equipment and second data representing the biometric identifier of the health care provider generated by the biometric scanner of the electronic device, the second data representing the biometric identifier of the health care provider being the same as the first data representing a biometric identifier of the health care provider; and an analyzing unit for analyzing the first transmission, the second transmission, and the third transmission, and preventing payment of a fraudulent claim by one or more of: preventing information from being entered into a billing form at the electronic device, preventing the submission of the billing form from the electronic device, or preventing acceptance of the billing form; and a database for storing the first transmission.

2. The computer-implemented system of claim 1, wherein the biometric scanner comprises a fingerprint scanner.

3. The computer-implemented system of claim 1, wherein the database stores the second transmission and the third transmission.

4. The computer-implemented system of claim 3, wherein the system is configured to analyze at least two of the first, second, and third transmissions with previously stored data for instances of fraud.

5. The computer-implemented system of claim 4, wherein the system is configured to analyze the first transmission to determine if a patient is attempting to obtain more than one of the prescribed durable medical equipment.

6. The computer-implemented system of claim 4, wherein the system is configured to analyze the second transmission to determine if a supplier is attempting to file a fraudulent claim.

7. The computer-implemented system of claim 1, wherein the communication unit is configured to receive information related to deceased individuals and the database is configured to store the information related to deceased individuals, the information including whether the deceased individual was a health care provider.

8. The computer-implemented system of claim 7, wherein the system is configured to analyze the first transmission and determine if the health care provider is deceased.

9. The computer-implemented system of claim 4, wherein the communication unit transmits authorization to pay the prescription after receipt of the third transmission.

10. A computer-implemented system for preventing submission and payment of fraudulent claims comprising:

an electronic device used by a health care provider, the electronic device including a biometric scanner for creating a biometric identifier of the health care provider;

a communication unit for receiving:

a first transmission prepared and transmitted by the electronic device comprising a prescription for durable medical equipment for a patient prepared by the electronic device and first data representing a biometric identifier of the health care provider generated by the biometric scanner of the electronic device, the first data representing the biometric identifier being generated to be uniquely included in the first transmission, a second transmission comprising notice of a claim by a durable medical equipment supplier for the prescribed durable medical equipment, and a third transmission prepared and transmitted by the electronic device comprising verification that the patient received the durable medical equipment and second data representing the biometric identifier of the health care provider generated by the biometric scanner of the electronic device, the second data representing the biometric identifier of the health care provider being the same as the first data representing a biometric identifier of the health care provider; and an analyzing unit for analyzing the first transmission, second transmission, and third transmission, and preventing payment of a fraudulent claim by one or more of: preventing information from being entered into a billing form at the electronic device, preventing the submission of the billing form from the electronic device, or preventing acceptance of the billing form; and a database for storing the prescription and the first data representing a biometric identifier of the health care provider, wherein the system is configured to analyze the prescription and the first data representing a biometric identifier of the health care provider with previously stored data to prevent submission and payment of a fraudulent claim for the durable medical equipment.

11. The computer-implemented system of claim 10, wherein the system is configured to analyze the prescription to determine if a patient is attempting to obtain more than one of the prescribed durable medical equipment.

12. The computer-implemented system of claim 10, wherein the system is configured to receive notification of a claim for the durable medical equipment for the patient and is configured to analyze the claim to determine if a supplier is attempting to file a fraudulent claim.

13. The computer-implemented system of claim 10, wherein the system is configured to analyze the prescription to determine if a health care provider is writing more prescriptions for durable medical than a statistically calculated maximum number.

14. The computer-implemented system of claim 10, wherein the communication unit is configured to receive information related to deceased individuals and the database is configured to store the information related to deceased individuals, the information including whether the deceased individual was a health care provider.

15. The computer-implemented system of claim 14, wherein the system is configured to analyze the prescription and determine if the health care provider is deceased.

16. A method for preventing submission and payment of fraudulent claims comprising:

receiving a transmission prepared and transmitted by an electronic device used by a health care provider in a computer-implemented system comprising a database, the transmission comprising a prescription for durable medical equipment for a patient and first data representing a biometric identifier of the health care provider generated by a biometric scanner included in the electronic device, the biometric identifier being generated to be uniquely included in the first transmission;

storing the prescription and the first data representing the biometric identifier in the database;

comparing the first data representing the biometric identifier of the health care provider with preexisting biometric identifier data stored in the database to authenticate the first data representing the biometric identifier of the health care provider;

receiving notice of a claim for the prescribed durable medical equipment;

receiving verification, prepared and transmitted by the electronic device, that the patient has received the prescribed durable medical equipment, the verification including second data representing a biometric identifier of the health care provider generated by the biometric scanner of the electronic device, the second data representing the biometric identifier of the health care provider being the same as the first data representing a biometric identifier of the health care provider; and upon authenticating the first data and receiving the verification, transmitting authorization to pay the claim; and upon failing to authenticate the first data or failing to receive the verification, preventing payment of a fraudulent claim by one or more of: preventing information from being entered into a billing form at the electronic device, preventing the submission of the billing form from the electronic device, or preventing acceptance of the billing form.

17. The method of claim 16, further comprising receiving notice from a durable medical equipment supplier that the prescription has been filled.

18. The method of claim 17, wherein the biometric identifier scanner is selected from the group consisting of a fingerprint scanner and a retinal scanner.

19. The method of claim 16, wherein the computer-implemented system further comprises a communication unit for receiving the transmission and transmitting the authorization to pay the claim.

* * * * *